(12) United States Patent
Philip

(10) Patent No.: US 10,117,922 B2
(45) Date of Patent: Nov. 6, 2018

(54) DENGUE VIRUS SPECIFIC MULTIPLE HLA BINDING T CELL EPITOPES FOR THE USE OF UNIVERSAL VACCINE DEVELOPMENT

(71) Applicant: Emergex Vaccines Holding Ltd., Abingdon (GB)

(72) Inventor: Ramila Philip, Ivyland, PA (US)

(73) Assignee: Emergex Vaccines Holding Ltd., Abingdon, Oxford (GB)

( * ) Notice: Subject to any disclaimer, the term of this patent is extended or adjusted under 35 U.S.C. 154(b) by 0 days.

(21) Appl. No.: 15/310,542

(22) PCT Filed: May 11, 2015

(86) PCT No.: PCT/US2015/030058
§ 371 (c)(1),
(2) Date: Nov. 11, 2016

(87) PCT Pub. No.: WO2015/175361
PCT Pub. Date: Nov. 19, 2015

(65) Prior Publication Data
US 2017/0119869 A1    May 4, 2017

Related U.S. Application Data

(60) Provisional application No. 61/992,396, filed on May 13, 2014.

(51) Int. Cl.
| | | |
|---|---|---|
| *A61K 39/00* | (2006.01) |
| *A61K 39/12* | (2006.01) |
| *A61K 39/395* | (2006.01) |
| *G01N 33/569* | (2006.01) |
| *A61K 48/00* | (2006.01) |
| *C12N 7/00* | (2006.01) |
| *C07K 14/005* | (2006.01) |

(52) U.S. Cl.
CPC ............ *A61K 39/12* (2013.01); *C07K 14/005* (2013.01); *C12N 7/00* (2013.01); *A61K 2039/572* (2013.01); *A61K 2039/70* (2013.01); *C12N 2770/24122* (2013.01); *C12N 2770/24134* (2013.01)

(58) Field of Classification Search
CPC ................ A61K 39/12; A61K 39/0011; A61K 2039/53; A61K 2039/505; C07K 14/005
See application file for complete search history.

(56) References Cited

U.S. PATENT DOCUMENTS

| | | | |
|---|---|---|---|
| 4,722,848 A | 2/1988 | Paoletti et al. |
| 5,635,363 A | 6/1997 | Altman et al. |
| 5,662,907 A | 9/1997 | Kubo et al. |
| 2011/0150914 A1 | 6/2011 | Shresta et al. |
| 2013/0064843 A1* | 3/2013 | Brusic .................... A61K 39/12 424/186.1 |
| 2013/0115617 A1* | 5/2013 | Wilson .................... A61K 35/17 435/7.1 |
| 2013/0202634 A1 | 8/2013 | Shresta et al. |
| 2014/0105925 A1* | 4/2014 | Philip .................... A61K 39/12 424/186.1 |

OTHER PUBLICATIONS

Osman et al., "Complete genome sequence analysis of dengue virus type 2 isolated in Brunei", (GenBank: ABW06614.1), Virus Research, 2008, 135:48-52.*
Posneft, D. N. et al., J.Biol.Chem., 263:1719-1725, (1988).
Weaver, S.C. and N. Vasilakis, Molecular evolution of dengue viruses: contributions of phylogenetics to understanding the history and epidemiology of the preeminent arboviral disease. Infect Genet Evol, 2009. 9(4): p. 523-40.
Whitehorn, J. and C.P. Simmons, The pathogenesis of dengue. Vaccine. 29(42): p. 7221-8.
Yacoub, S., J. Mongkolsapaya, and G. Screaton, The pathogenesis of dengue. Curr Opin Infect Dis. 26(3): p. 284-9.
Malavige, G.N. and G.S. Ogg, T cell responses in dengue viral infections. J Clin Virol. 58(4): p. 605-11.
Weiskopf, D. and A. Sette, T-Cell Immunity to Infection with Dengue Virus in Humans. Front Immunol. 5: p. 93.
Bhatt, S., et al., The global distribution and burden of dengue. Nature. 496(7446): p. 504-7.
Mathew, A. and A.L. Rothman, Understanding the contribution of cellular immunity to dengue disease pathogenesis. Immunol Rev, 2008. 225: p. 300-13.
Bukowski, J.F., et al., Dengue virus-specific cross-reactive CD8+ human cytotoxic T lymphocytes. J Virol, 1989. 63(12): p. 5086-91.
Simmons, C.P. et al., Early T-cell responses to dengue virus epitopes in Vietnamese adults with secondary dengue virus infections. J Virol, 2005. 79(9): p. 5665-75.

(Continued)

*Primary Examiner* — Barry A Chestnut
(74) *Attorney, Agent, or Firm* — Joseph F. Aceto, Esq.

(57) ABSTRACT

Dengue Fever (DF) and Dengue Hemorrhagic Fever (DHF) are significant global public health problems and understanding the overall immune response to infection will contribute to appropriate management of the disease and its potentially severe complications. Live attenuated and sub-unit vaccine candidates, which are under clinical evaluation, induce primarily an antibody response to the virus and minimal cross-reactive T cell responses. Currently, there are no available tools to assess protective T cell responses during infection or post vaccination. Herein, we report novel, naturally processed and presented MHC class I restricted epitopes, a subset of which binds to and activates T cells in both an HLA-A2 and HLA-A24 restricted manner. We show that epitope specific T cells can be activated in vivo in transgenic mice and in vitro in seropositive and seronegative individuals and that these T cells are functional, recognizing peptide pulsed and dengue virus infected cells in a pro-inflammatory and cytotoxic manner. These epitopes have potential as new informational and diagnostic tools to characterize T cell immunity in Dengue virus (DV) infection, and may serve as a universal vaccine candidate complementary to current vaccines in trial.

6 Claims, 2 Drawing Sheets
Specification includes a Sequence Listing.

(56) References Cited

OTHER PUBLICATIONS

Mathew, A., et al., Dominant recognition by human CD8+ cytotoxic T lymphocytes of dengue virus nonstructural proteins NS3 and NS1.2a. J Clin Invest, 1996. 98(7): p. 1684-91.
Hatch, S. et al., Intracellular cytokine production by dengue virus-specific T cells correlates with subclinical secondary infection. J Infect Dis. 203(9): p. 1282-91.
Yauch, L.E. et al., A protective role for dengue virus-specific CD8+ T cells. J Immunol, 2009. 182(8): p. 4865-73.
Gil, L., et al., The cellular immune response plays an important role in protecting against dengue virus in the mouse encephalitis model. Viral Immunol, 2009. 22(1): p. 23-30.
Testa, J.S., et al., Conserved MHC class I-presented dengue virus epitopes identified by immunoproteomics analysis are targets for cross-serotype reactive T-cell response. J Infect Dis. 205(4): p. 647-55.
Wan, S.W., et al., Current progress in dengue vaccines. J Biomed Sci. 20: p. 37.
Guirakhoo, F., et al., Viremia and immunogenicity in nonhuman primates of a tetravalent yellow fever-dengue chimeric vaccine: genetic reconstructions, dose adjustment, and antibody responses against wild-type dengue virus isolates. Virology, 2002. 298(1): p. 146-59.
Dayan, G.H., et al., Immunogenicity and safety of a recombinant tetravalent dengue vaccine in children and adolescents ages 9-16 years in Brazil. Am J Trop Med Hyg. 89(6): p. 1058-65.
Lindow, J.C., et al., Vaccination of volunteers with low-dose, live-attenuated, dengue viruses leads to serotype-specific immunologic and virologic profiles. Vaccine. 31(33): p. 3347-52.
Johnson, B.W., et al., Growth characteristics of ChimeriVax-DEN2 vaccine virus in Aedes aegypti and Aedes albopictus mosquitoes. Am J Trop Med Hyg, 2002. 67(3): p. 260-5.
Vazquez, S., et al., Immune response to synthetic peptides of dengue prM protein. Vaccine, 2002. 20(13-14): p. 1823-30.

de Melo, A.B., et al., T-cell memory responses elicited by yellow fever vaccine are targeted to overlapping epitopes containing multiple HLA-I and -II binding motifs. PLoS Negl Trop Dis. 7(1): p. e1938.
Rothman, A.L., Dengue: defining protective versus pathologic immunity. J Clin Invest, 2004. 113(7): p. 946-51.
Sidney, J., et al., HLA class I supertypes: a revised and updated classification. BMC Immunol, 2008. 9: p. 1.
Shetty, V., et al., Quantitative immunoproteomics analysis reveals novel MHC class I presented peptides in cisplatin-resistant ovarian cancer cells. J Proteomics. 75(11): p. 3270-90.
Shetty, V., et al., MHC class I-presented lung cancer-associated tumor antigens identified by immunoproteomics analysis are targets for cancer-specific T cell response. J Proteomics. 74(5): p. 728-43.
Testa, J.S., et al., MHC class I-presented T cell epitopes identified by immunoproteomics analysis are targets for a cross reactive influenza-specific T cell response. PLoS One. 7(11): p. e48484.
Weiskopf, D., et al., Comprehensive analysis of dengue virus-specific responses supports an HLA-linked protective role for CD8+ T cells. Proc Natl Acad Sci U S A. 110(22): p. E2046-53.
Khan, A.M., et al., Conservation and variability of dengue virus proteins: implications for vaccine design. PLoS Negl Trop Dis, 2008. 2(8): p. e272.
Olsen, L.R., et al., Conservation analysis of dengue virus T-cell epitope-based vaccine candidates using Peptide block entropy. Front Immunol. 2: p. 69.
Betts, M.R., et al., Sensitive and viable identification of antigen-specific CD8+ T cells by a flow cytometric assay for degranulation. J Immunol Methods, 2003. 281(1-2): p. 65-78.
Mittendorf, E.A., et al., Evaluation of the CD107 cytotoxicity assay for the detection of cytolytic CD8+ cells recognizing HER2/neu vaccine peptides. Breast Cancer Res Treat, 2005. 92(1): p. 85-93.
Parmigiani, A., et al., Impaired antibody response to influenza vaccine in HIV-infected and uninfected aging women is associated with immune activation and inflammation. PLoS One. 8(11): p. e79816.
Nieminen, J.K., et al., Dendritic cells from Crohn's disease patients show aberrant STAT1 and STAT3 signaling. PLoS One. 8(8): p. e70738.

* cited by examiner

SEQUENCE LISTING

```
<160> NUMBER OF SEQ ID NOS: 16

<210> SEQ ID NO 1
<211> LENGTH: 10
<212> TYPE: PRT
<213> ORGANISM: Homo sapiens

<400> SEQUENCE: 1

Ala Met Leu Cys Ile Pro Asn Ala Ile Ile
1               5                   10

<210> SEQ ID NO 2
<211> LENGTH: 9
<212> TYPE: PRT
<213> ORGANISM: Homo sapiens
```

<400> SEQUENCE: 2

Leu Leu Cys Val Pro Asn Ile Met Ile
1               5

<210> SEQ ID NO 3
<211> LENGTH: 8
<212> TYPE: PRT
<213> ORGANISM: Homo sapiens

<400> SEQUENCE: 3

Ala Phe Ile Ala Phe Val Arg Phe
1               5

<210> SEQ ID NO 4
<211> LENGTH: 9
<212> TYPE: PRT
<213> ORGANISM: Homo sapiens

<400> SEQUENCE: 4

Met Ile Ile Val Asp Glu Ala His Phe
1               5

<210> SEQ ID NO 5
<211> LENGTH: 8
<212> TYPE: PRT
<213> ORGANISM: Homo sapiens

<400> SEQUENCE: 5

Ile Val Phe Phe Val Leu Met Met
1               5

<210> SEQ ID NO 6
<211> LENGTH: 10
<212> TYPE: PRT
<213> ORGANISM: Homo sapiens

<400> SEQUENCE: 6

Leu Leu Thr Ala Ile Ala Pro Ser Met Ala
1               5                   10

<210> SEQ ID NO 7
<211> LENGTH: 10
<212> TYPE: PRT
<213> ORGANISM: Homo sapiens

<400> SEQUENCE: 7

Leu Val Met Val Gly Val Ile Thr Leu Tyr
1               5                   10

<210> SEQ ID NO 8
<211> LENGTH: 10
<212> TYPE: PRT
<213> ORGANISM: Homo sapiens

<400> SEQUENCE: 8

Val Leu Thr Gly Ala Thr Glu Ile Gln Thr
1               5                   10

<210> SEQ ID NO 9
<211> LENGTH: 10
<212> TYPE: PRT
<213> ORGANISM: Homo sapiens

<400> SEQUENCE: 9

Val Leu Val Gly Phe Val Thr Leu Tyr Leu
1               5                   10

<210> SEQ ID NO 10
<211> LENGTH: 9
<212> TYPE: PRT
<213> ORGANISM: Homo sapiens

<400> SEQUENCE: 10

Val Val Ile Phe Ile Leu Leu Met Leu
1               5

<210> SEQ ID NO 11
<211> LENGTH: 9
<212> TYPE: PRT
<213> ORGANISM: Homo sapiens

<400> SEQUENCE: 11

Lys Leu Cys Glu Asp Thr Ile Thr Tyr
1               5

<210> SEQ ID NO 12
<211> LENGTH: 10
<212> TYPE: PRT
<213> ORGANISM: Homo sapiens

<400> SEQUENCE: 12

Lys Tyr Gln Leu Ala Val Thr Ile Met Thr
1               5                   10

<210> SEQ ID NO 13
<211> LENGTH: 11
<212> TYPE: PRT
<213> ORGANISM: Homo sapiens

<400> SEQUENCE: 13

Gly Arg Leu Ile Thr Ala Asn Pro Met Val Thr
1               5                   10

<210> SEQ ID NO 14
<211> LENGTH: 9
<212> TYPE: PRT
<213> ORGANISM: Homo sapiens

<400> SEQUENCE: 14

Thr Leu Ile Leu Ala Pro Thr Arg Val
1               5

<210> SEQ ID NO 15
<211> LENGTH: 9
<212> TYPE: PRT
<213> ORGANISM: Homo sapiens

<400> SEQUENCE: 15

Ile Thr Leu Leu Cys Leu Ile Pro Thr
1               5

<210> SEQ ID NO 16
<211> LENGTH: 9
<212> TYPE: PRT
<213> ORGANISM: Homo sapiens

```
<400> SEQUENCE: 16

Ile Thr Leu Leu Val Lys Leu Ala Leu
1               5
```

DENGUE VIRUS SPECIFIC MULTIPLE HLA BINDING T CELL EPITOPES FOR THE USE OF UNIVERSAL VACCINE DEVELOPMENT

CROSS REFERENCE TO RELATED APPLICATIONS

This application is the US national application of PCT/US2015/030058, filed on 11 May 2015 and which claims priority to U.S. Provisional Application No. 61/992,396, filed on 13 May 2014, the disclosure of which is herein incorporated by reference in its entirety.

This invention was made with Government support under Grant Number A 1062177 awarded by the National Institutes of Health, The Government has certain rights in the invention.

FIELD OF THE INVENTION

The present invention relates generally to the field of immunogens whose structures incorporate polypeptides comprising MHC class I restricted epitopes, a subset of which binds to and activates T cells in both an HLA-A2 and HLA-A24 restricted manner.

BACKGROUND OF THE INVENTION

Dengue virus (DENV) is a member of the Flaviviridae family of viruses characterized by a single stranded RNA genome enclosed within a spherical enveloped virion. Four distinct serotypes of DENV exist (DENV1-4; 65% conservation), each capable of causing disease following transmission by the arthropod vectors *Aedes aegypti* or *Aedes albopictus*. Although the large majority of primary infections are asymptomatic, DENV infections can cause a flu-like illness characterized by fever, fatigue, muscle pains, and rash and, in a small proportion of infected individuals, a severe form of disease called dengue hemorrhagic fever. Immunological memory protects individuals from reinfection with the same but not distinct serotypes and the more severe forms of disease most often occur during secondary infection with a different serotype. Current estimates indicate between 100 and 300 [6] million dengue virus infections occur throughout the world each year and people in over 100 countries are currently at risk of being infected with DENV. Therefore, dengue virus is now considered a "priority pathogen" by multiple governing bodies.

CD8$^+$ T cells (CTLs) are a major contributor of protection against dengue virus infection. DENV specific CD8$^+$ T cells have been detected in patients after natural infection and attempts at vaccination with some level of cross-reactivity between strains. Studies in children indicated that CD8$^+$ T mediated secretion of IFN-gamma and TNF-alpha was more robust in children with asymptomatic, or subclinical, infections compared to those with symptomatic or severe disease. Likewise, in murine models of dengue virus infection, CD8$^+$ T cells expanded robustly, secreted pro-inflammatory cytokines, possessed cytotoxic capabilities and their depletion prior to infection significantly altered the course of infection. Together, these studies indicate that successful clearance of and protection from secondary dengue virus infections requires a multifunctional and cross-reactive CD8$^+$ T cell response. Additionally, CD8$^+$ T cells directed against each of the viral proteins have been detected indicating that broad dengue specific T cell responses may also be necessary for protection.

To date, no specific dengue virus treatments or vaccines have been approved for use in infected or at risk individuals. Multiple vaccine strategies have been attempted and a number are in various stages of development including live attenuated viruses, inactivated viruses, and peptide based vaccines but most have achieved limited success. Interestingly, live-attenuated vaccine strategies induce the most robust B and T cell responses after vaccination indicating that efficient protection may be achieved through activation of B and T cells through alternative means. Therefore, determining the peptide epitopes that are naturally generated by antigen presenting cells during a dengue virus infection would allow for the development of other vaccine formulations (i.e. peptide based) that can induce robust and cross reactive T cell responses. The major caveat of a peptide identification approach, however, is the variability in HLA molecules that exists worldwide. The large majority of dengue infections occur in dengue endemic regions (i.e. Brazil, Asia) where the HLA-A24 molecule is most common (http://www.allelefrequencies.net/). However, with the recent emergence of dengue virus infections in other regions of the world, successful vaccine formulations must include peptides capable of binding multiple HLA alleles. For example, peptides restricted to the HLA-A2 allele and peptides restricted to the HLA-A24 allele must be included in the same vaccine formulation. Interestingly, peptides generated by the processing machinery are capable of binding to multiple HLA class I molecules; this property has allowed HLA molecules to be categorized into supertypes. Peptides that bind to one member of the MHC superfamily are likely to bind to other members of the same family. This property makes it possible to identify single peptides that bind to and induce T cell activation in multiple different MHC class I settings.

BRIEF SUMMARY OF THE INVENTION

The inventor in the present invention discovered HLA-A2 and A24 binding dengue virus epitopes activates T cells in both an HLA-A2 and HLA-A24 restricted manner. The epitope specific T cells are activated in seropositive and seronegative individuals and these T cells are functional, recognizing peptide pulsed and dengue virus infected cells in a pro-inflammatory and cytotoxic manner.

Using an immunoproteomic approach to peptide epitope discovery, several significant advantages over prior approaches are described. First, the approach allows for identification of epitopes that are present on the surface of the infected cell. Second, the immunoproteomic approach allows for the identification of peptides that are capable of binding to multiple HLA molecules. Finally, peptides binding to different HLA molecules can be identified from the same preparation of infected cells without increasing experimental difficulty. All of these advantages are crucial for vaccine formulations as the distribution of these alleles varies significantly.

DETAILED DESCRIPTION OF THE INVENTION

Definitions

Figure 1:
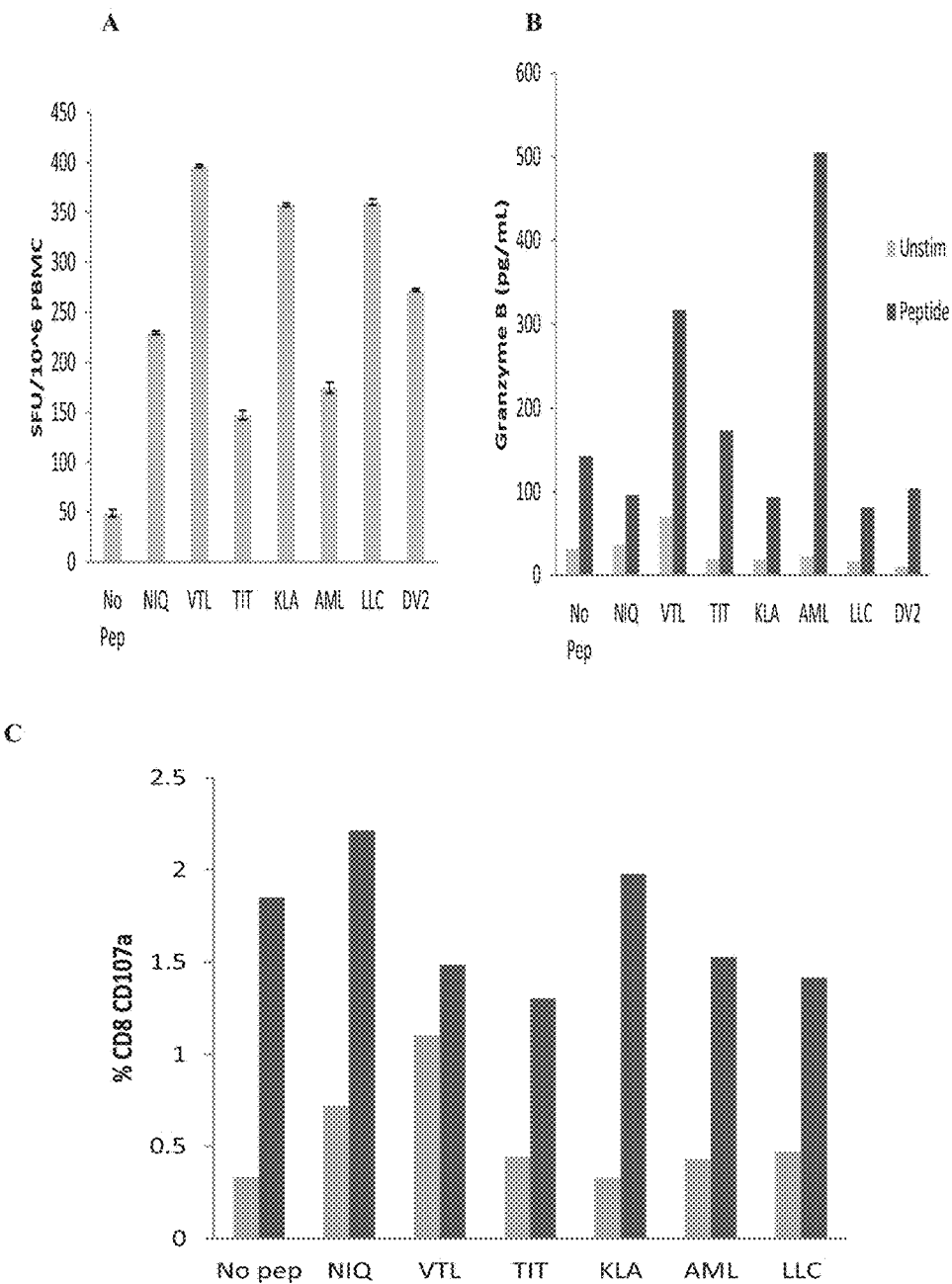
FIG. 1. HLA-A2 and A24 binding dengue virus specific MHC class I epitopes stimulate CD8+ T cells in vitro. (A.) HLA-A2 restricted CTLs directed against the peptides (peptides are represented as first 3 residues of the sequence) were generated using peripheral blood from a seronegative donor. PBMCs containing the epitope specific CTLs were harvested, washed, and cultured with the peptide pulsed DENV-2 infected cells overnight in an IFN-gamma ELISpot assay. (B). Identical cultures were set up as in (A) but in 96 well round bottom plates. The next day, supernatant was harvested and used to detect cytolytic activity (B) and the cells were analyzed for the marker of degranulation, CD107a (C.)

As used herein and except as noted otherwise, all terms are defined as given below. The term "peptide" is used herein to designate a series of amino acid residues, connected one to the other typically by peptide bonds between the alpha-amino and carbonyl groups of the adjacent amino acids. The peptides are typically 9 amino acids in length, but can be as short as 8 amino acids in length, and as long as 14 amino acids in length. The series of amino acids are consider an "oligopeptide" when the amino acid length is greater than about 14 amino acids in length, typically up to about 30 to 40 residues in length. When the amino acid residue length exceeds 40 amino acid residues, the series of amino acid residues is termed "polypeptide".

A peptide, oligopeptide, polypeptide, protein, or polynucleotide coding for such a molecule is "immunogenic" and thus an immunogen within the present invention if it is capable of inducing an immune response. In the present invention, immunogenicity is more specifically defined as the ability to induce a CTL-mediated response. Thus, an immunogen would be a molecule that is capable of inducing an immune response, and in the present invention, a molecule capable of inducing a CTL response. An immunogen may have one or more isoforms or splice variants that have equivalent biological and immunological activity, and are thus also considered for the purposes of this invention to be immunogenic equivalents of the original, natural polypeptide.

A T cell "epitope" is a short peptide molecule that binds to a class I or II MHC molecule and that is subsequently recognized by a T cell. T cell epitopes that bind to class I MHC molecules are typically 8-14 amino acids in length, and most typically 9 amino acids in length. T cell epitopes that bind to class II MHC molecules are typically 12-20 amino acids in length. In the case of epitopes that bind to class 11 MHC molecules, the same T cell epitope may share a common core segment, but differ in the length of the carboxy- and amino-terminal flanking sequences due to the fact that ends of the peptide molecule are not buried in the structure of the class II MHC molecule peptide-binding cleft as they are in the class I MHC molecule peptide-binding cleft.

The present invention describes a novel, naturally processed and presented MHC class I restricted epitopes, a subset of which binds to and activates T cells in both an HLA-A2 and HLA-A24 restricted manner. The epitope specific T cells can be activated in vivo in transgenic mice and in vitro in seropositive and seronegative individuals and these T cells are functional, recognizing peptide pulsed and dengue virus infected cells in a pro-inflammatory and cytotoxic manner. These epitopes have potential as new informational and diagnostic tools to characterize T cell immunity in Dengue virus (DV) infection, and may serve as a universal vaccine candidate complementary to current vaccines in trial.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence.

The term "coding region" refers to that portion of a gene that either naturally or normally codes for the expression product of that gene in its natural genomic environment, i.e., the region coding in vivo for the native expression product of the gene. The coding region can be from a normal, mutated or altered gene, or can even be from a DNA sequence, or gene, wholly synthesized in the laboratory using methods well known to those of skill in the art of DNA synthesis.

The term "nucleotide sequence" refers to a heteropolymer of deoxyribonucleotides. The nucleotide sequence encoding for a particular peptide, oligopeptide, or polypeptide may be naturally occurring or they may be synthetically constructed.

The term "fragment," when referring to a coding sequence, means a portion of DNA comprising less than the complete coding region whose expression product retains essentially the same biological or immunological function or activity as the expression product of the complete coding region.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art.

The term "active fragment" means a fragment that generates an immune response (i.e., has immunogenic activity) when administered, alone or optionally with a suitable adjuvant, to an animal, such as a mammal, for example, a human, and also including a rabbit or a mouse, such immune response taking the form of stimulating a CTL response within the recipient, such as a human. Alternatively, the "active fragment" may also be used to induce a CTL response in vitro.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, such terms refer to the products produced by treatment of said polynucleotides with endonucleases.

In accordance with the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=100[1−(C/R)]

wherein C is the number of differences between the Reference Sequence and the Compared Sequence over the length of alignment between the Reference Sequence and the Compared Sequence wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

DESCRIPTION

The present invention embodies generally immunogens and immunogenic compositions, and methods of use thereof, for the prevention, treatment, and diagnosis of dengue virus infection. The immunogens comprise proteins or polypeptides whose amino acid sequences includes one or more epitopic oligopeptides with sequences selected from the group SEQ ID NO: 1-16.

One embodiment of the present invention includes compositions for DV peptides, subsequence and portions thereof, nucleic acid sequences encoding DV peptides, subsequences and portions thereof, and host cells expressing DV peptides, subsequences and portions thereof. One particular aspect of the subsequence or portion of the DV polypeptide sequence includes epitopic peptides. These embodiments further incorporate useful pharmaceutical compositions such as, but not limited to, an adjuvant (e.g., Freund's complete or incomplete adjuvant) or administration with traditional prophylactic viral vaccine formulations (e.g., live attenuated viruses, inactivated viruses, recombinant proteins, chimeric viruses, DNA vaccines, and synthetic peptides).

The invention includes kits that contain DV peptides, subsequences and portions thereof, compositions, that optionally include instructions for treating (prophylactic or therapeutic), vaccinating or immunizing a subject against a DV infection, or treating (prophylactic or therapeutic) a subject having or at risk of having a Dengue virus infection or pathology.

In accordance with further embodiments of the invention, methods for treating a subject having a DV infection (acute) are provided. In one embodiment, a method includes administering to a subject in need thereof an amount of a DV peptide or epitopic peptide, subsequence or portion thereof, sufficient to treat the subject for the pathogen infection.

In accordance with further embodiments of the invention, there are provided prophylactic methods including methods of vaccinating and immunizing a subject against a DV infection (acute) such as, but not limited to, protecting a subject against a DV infection to decrease or reduce the probability of a DV infection or pathology in a subject or to decrease or reduce susceptibility of a subject to a DV infection or pathology or to inhibit or prevent a DV infection in a subject.

In accordance with further embodiments of the present invention specific oligopeptide sequences are disclosed with amino acid sequences shown in SEQ ID NO: 1-16 representing epitopic peptides (i.e. immunogenic oligopeptide sequences).

While the use of specific peptides is restricted to use in patients having certain HLA types or HLA supertypes, there is no such restriction on the use of the parent protein as an immunogen. When the parent protein or immunogen is presented to the antigen processing pathway, it will be appropriately fragmented, processed and presented in the context of HLA type(s) present in the patient.

The polypeptides forming the immunogens of the present invention have amino acid sequences that comprise at least one stretch, possibly two, or more stretches of about 8 to or up to 14 residues in length and which stretches differ in amino acid sequence from the sequences of SEQ ID NO: 1-16 by no more than about 1 amino acid residue, preferably a conservative amino acid residue, especially amino acids of the same general chemical character, such as where they are hydrophobic amino acids.

These polypeptides are of any desired length so long as they have immunogenic activity in that they are able, under a given set of desirable conditions, to elicit in vitro or in vivo the activation of cytotoxic T lymphocytes (CTLs) (i.e., a CTL response) against a presentation of DV specific protein. The proteins and polypeptides forming the immunogens of the present invention can be naturally occurring or synthesized chemically.

The present invention further embodies an isolated polypeptide, especially one having immunogenic activity, the sequence of which comprises within it one or more stretches comprising any 2 or more of the sequences of SEQ ID NO: 1-16 and in any relative quantities and wherein said sequences may differ by one amino acid residues from the sequences of SEQ ID NO: 1-16 in any given stretch of 8 to 10, or up to 14 amino acid residues. In one embodiment, combinations and permutations of the epitopic sequences disclosed herein may be part of an immunogen of the present invention or of such a polypeptide so long as any such polypeptide comprises at least 2 such epitopes, whether such epitopes are different or the same. Thus, in a specific embodiment, a polypeptide of the present invention may comprise 2 copies of the sequence of SEQ ID NO: 2 at some point or points within its length. Of course, any combinations and permutations of the epitopes disclosed herein, as long as they are present at least two in number in such polypeptides, are expressly contemplated.

All of the epitopic peptides of SEQ ID NO: 1 through 16 are derived from proteins expressed by DV infected cells and sequences.

The immunogens of the present invention can be in the form of a composition of one or more of the different immunogens and wherein each immunogen is present in any desired relative abundance. Such compositions can be homogeneous or heterogeneous with respect to the individual immunogenic peptide components present therein, having only one or more than one of such peptides.

The oligopeptides and polypeptides useful in practicing the present invention may be derived by fractionation of naturally occurring proteins by methods such as protease treatment, or they may be produced by recombinant or synthetic methodologies that are well known and clear to the skilled artisan. The polypeptide may comprise a recombinant or synthetic polypeptide having at least one of SEQ ID NO: 1-16. Thus, oligopeptides and polypeptides of the present invention have at least one immunogenic peptides within the amino acid sequence of said oligopeptides and polypeptides, and said immunogenic peptides, or epitopes, which are the same or different, or may have any number of such sequences wherein some of them are identical to each other in amino acid sequence and said epitopic sequences occur in any order within said immunogenic polypeptide sequence. The location of such sequences within the sequence of a polypeptide forming an immunogen may affect relative immunogenic activity. In addition, immunogens of the present invention may comprise more than one protein comprising the amino acid sequences disclosed herein. Such polypeptides may be part of a single composition or may themselves be covalently or non-covalently linked to each other.

The immunogenic peptides disclosed herein may also be linked directly to, or through a spacer or linker to: an immunogenic carrier such as serum albumin, tetanus toxoid, keyhole limpet hemocyanin, dextran, or a recombinant virus particle; an immunogenic peptide known to stimulate a T helper cell type immune response; a cytokine such as interferon gamma or GMCSF; a targeting agent such as an antibody or receptor ligand; a stabilizing agent such as a lipid; or a conjugate of a plurality of epitopes to a branched lysine core structure, such as the so-called "multiple antigenic peptide" described in (Posneft, D. N. et al., J. Biol. Chem., 263:1719-1725, (1988)); a compound such as polyethylene glycol to increase the half-life of the peptide; or additional amino acids such as a leader or secretory sequence, or a sequence employed for the purification of the mature sequence. Spacers and linkers typically comprise relatively small, neutral molecules. In addition, such linkers need not be composed of amino acids but any oligomeric structures will do as well so long as they provide the correct spacing so as to optimize the desired level of immunogenic activity of the immunogens of the present invention. The immunogen may therefore take any form that is capable of eliciting a CTL response.

In addition, the immunogenic peptides of the present invention may be part of an immunogenic structure via attachments other than conventional peptide bonds. Thus, any manner of attaching the peptides of the invention to an immunogen of the invention, such as an immunogenic polypeptide as disclosed herein, could provide an immunogenic structure as claimed herein. Thus, immunogens, such as proteins, oligopeptides and polypeptides of the invention, are structures that contain the peptides disclosed according to the present invention but such immunogenic peptides may not necessarily be attached thereto by the conventional means of using ordinary peptide bounds. The immunogens of the present invention simply contain such peptides as part of their makeup, but how such peptides are to be combined to form the final immunogen is through any means known in the art.

The peptides that are naturally processed and bound to a class I MHC molecule, and which are recognized by the DV-specific CTL, need not be the optimal peptides for stimulating a CTL response. Thus, the ability to modify a peptide such that it more readily induces a CTL response is considered. Generally, the peptides may be modified at amino acid residues that are predicted to interact with the class 1 MHC molecule, in which case the goal is to create a peptide that has a higher affinity for the class I MHC molecule than does the original peptide. The peptides can be modified at amino acid residues that are predicted to interact with the T cell receptor on the CTL, in which case the goal is to create a peptide that has a higher affinity for the T cell receptor than does the original peptide. Both of these types of modifications can result in a variant peptide that is related to an original peptide, but which is better able to induce a CTL response than is the original peptide as selected from SEQ ID NO: 1-16.

The original peptides disclosed herein can be further modified by the substitution of one or more residues at different, possibly selective, sites within the peptide chain. Such substitutions may be conservative where, for example, one amino acid is replaced by an amino acid of similar structure and characteristics, or a hydrophobic amino acid is replaced by another hydrophobic amino acid. Conservative substitutions are herein defined as exchanges within one of the following five groups: Group 1—small aliphatic, nonpolar or slightly polar residues (Ala, Ser, Thr, Pro, Gly); Group 2—polar, negatively charged residues and their amides (Asp, Asn, Glu, Gin); Group 3—polar, positively charged residues (His, Arg, Lys); Group 4—large, aliphatic, nonpolar residues (Met, Leu, Ile, Val, Cys); and Group 4—large, aromatic residues (Phe, Tyr, Trp).

Less conservative substitutions or even highly non-conservative replacements are also considered since chemical effects are not totally predictable.

Based on cytotoxicity assays, an epitope is considered substantially identical to the reference peptide if it has at least 10% of the antigenic activity of the reference peptide as defined by the ability of the substituted peptide to reconstitute the epitope recognized by a CTL in comparison to the reference peptide. Thus, when comparing the lytic activity in the linear portion of the effector:target curves with equimolar concentrations of the reference and substituted peptides, the observed percent specific killing of the target cells incubated with the substituted peptide should be equal to that of the reference peptide at an effector:target ratio that is no greater than 10-fold above the reference peptide effector:target ratio at which the comparison is being made.

It should be appreciated that an immunogen may consist only of a peptide from SEQ ID NO: 1-16, or comprise a peptide of SEQ ID NO: 1-16, or comprise a plurality of peptides selected from SEQ ID NO: 1-16, or comprise a polypeptide that itself comprises one or more of the epitopic peptides of SEQ ID NO: 1-16.

The immunogenic peptides and polypeptides of the invention can be prepared synthetically, by recombinant DNA technology, or they can be isolated from natural sources such as infected cells expressing the original protein product.

The polypeptides and oligopeptides disclosed herein can be synthesized in solution or on a solid support in accordance with conventional techniques. Various automated peptide synthesizers are commercially available and can be used in accordance with known protocols. Fragments of polypeptides of the invention can also be synthesized as intermediates in the synthesis of a larger polypeptide.

Well known procedures that use recombinant DNA technology may be employed wherein a nucleotide sequence encoding an immunogenic peptide or polypeptide of interest is inserted into an expression vector, transformed or transfected into an appropriate host cell, and cultivated under conditions suitable for expression. Thus, recombinantly produced peptides or polypeptides can be used as the immunogens of the invention.

The coding sequences for peptides of the length contemplated herein can be synthesized on commercially available automated DNA synthesizers using protocols that are well known in the art. The coding sequences can also be modified such that a peptide or polypeptide will be produced that incorporates a desired amino acid substitution. The coding sequence can be provided with appropriate linkers, be ligated into suitable expression vectors that are commonly available in the art, and the resulting DNA or RNA molecule can be transformed or transfected into suitable hosts to produce the desired fusion protein. A number of such vectors and suitable host systems are available, and their selection is left to the skilled artisan. For expression of the fusion proteins, the coding sequence will be provided with operably linked start and stop codons, promoter and terminator regions, and a replication system to provide an expression vector for expression in the desired host cell. For example, promoter sequences compatible with bacterial hosts are provided in plasmids containing convenient restriction sites for insertion of the desired coding sequence. The resulting expression vectors are transformed into suitable bacterial hosts. Yeast, insect, and mammalian host cells may also be used, employing suitable vectors and control sequences.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In one embodiment, the construct further comprises regulatory sequences, including, for example, a promoter, operably linked to the sequence, essentially any vectors and promoters known to those of skill in the art are considered.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. Such cells can routinely be utilized for assaying CTL activity by having said genetically engineered, or recombinant, host cells express the immunogenic peptides of the present invention.

Various mammalian cell culture systems can also be employed to express recombinant protein. Examples of mammalian expression systems include the COS-7 lines of monkey kidney fibroblasts, and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. High performance liquid chromatography (HPLC) can be employed for final purification steps.

The immunogenic peptides of the present invention may be used to elicit CTLs ex vivo from either healthy individuals or from DV infected individuals. Such responses are induced by incubating in tissue culture the individual's CTL precursor lymphocytes together with a source of antigen presenting cells and the appropriate immunogenic peptide.

One embodiment of the present invention is directed to a process for treating a subject with infection characterized by infected cells expressing any class I MHC molecule and an epitope of SEQ ID NO: 1-16, whereby the CTLs are produced in vitro and are specific for the epitope or original protein and are administered in an amount sufficient to destroy the infected cells through direct lysis or to effect the destruction of the infected cells indirectly through the elaboration of cytokines.

In addition to their use for therapeutic or prophylactic purposes, the immunogenic peptides of the present invention are useful as screening and diagnostic agents. Thus, the immunogenic peptides of the present invention, together with modern techniques of CTL screening, make it possible to screen patients for the presence of T cells specific for these peptides as a test for DV infection, exposure and immune response. The results of such screening may help determine the efficacy of proceeding with the regimen of treatment disclosed herein using the immunogens of the present invention.

The oligopeptides of the invention, such as SEQ ID NO: 1-16, can also be used to prepare class I MHC tetramers or pentamers which can be used in conjunction with flow cytometry to quantitate the frequency of peptide-specific CTL that are present in a sample of lymphocytes from an individual. Specifically, for example, class I MHC molecules comprising peptides of SEQ ID NO: 1-16, would be combined to form tetramers as exemplified in U.S. Pat. No. 5,635,363. Said tetramers would find use in monitoring the frequency of CTLs in the peripheral blood or lymph nodes of an individual who is vaccinated or undergoing immunotherapy with the peptides, proteins, or polynucleotides of the invention, and it would be expected that successful immunization would lead to an increase in the frequency of the peptide-specific CTL.

Alternatively, the immunogenic peptides disclosed herein, as well as functionally similar homologs thereof, may be used to screen a sample for the presence of CTLs that specifically recognize the corresponding epitopes. The lymphocytes to be screened in this assay will normally be obtained from the peripheral blood, but lymphocytes can be obtained from other sources, including lymph nodes, spleen, and body fluids. The peptides of the present invention may then be used as a diagnostic tool to evaluate the efficacy of the immunotherapeutic treatments disclosed herein. Thus, the in vitro generation of CTL as described above would be used to determine if patients are likely to respond to the peptide in vivo. Similarly, the in vitro generation of CTL could be done with samples of lymphocytes obtained from the patient before and after treatment with the peptides. Successful generation of CTL in vivo should then be recognized by a correspondingly easier ability to generate peptide-specific CTL in vitro from lymphocytes obtained following treatment in comparison to those obtained before treatment.

As stated above, a prophylactic or therapeutic vaccine in accordance with the present invention may include one or more of the hereinabove described polypeptides or active fragments thereof, or a composition, or pool, of immunogenic peptides disclosed herein. When employing more than one polypeptide or active fragment, such as two or more polypeptides and/or active fragments may be used as a physical mixture or as a fusion of two or more polypeptides or active fragments. The fusion fragment or fusion polypeptide may be produced, for example, by recombinant techniques or by the use of appropriate linkers for fusing previously prepared polypeptides or active fragments.

The immunogenic molecules of the invention, including vaccine compositions, may be utilized according to the present invention for purposes of preventing, suppressing or treating diseases causing the expression of the immunogenic peptides disclosed herein, such as where the antigen is being expressed by DV infected cells. As used in accordance with the present invention, the term "prevention" relates to a process of prophylaxis in which an animal, especially a mammal, and most especially a human, is exposed to an immunogen of the present invention prior to the induction or onset of the disease process. This could be done where an individual is at high risk for DV infection based on the living or travel to the DV endemic areas. Alternatively, the immunogen could be administered to the general population as is frequently done for any infectious diseases. Alternatively, the term "suppression" is often used to describe a condition wherein the disease process has already begun but obvious symptoms of said condition have yet to be realized. Thus, the cells of an individual may have been infected but no outside signs of the disease have yet been clinically recognized. In either case, the term prophylaxis can be applied to encompass both prevention and suppression. Conversely, the term "treatment" is often utilized to mean the clinical application of agents to combat an already existing condition whose clinical presentation has already been realized in a patient. This would occur where an individual has already been diagnosed as having confirmed DV infection.

It is understood that the suitable dosage of an immunogen of the present invention will depend upon the age, sex, health, and weight of the recipient, the kind of concurrent treatment, if any, the frequency of treatment, and the nature of the effect desired. However, the most preferred dosage can be tailored to the individual subject, as determined by the researcher or clinician. The total dose required for any given treatment will commonly be determined with respect to a standard reference dose as set by a manufacturer, such as is commonly done with vaccines, such dose being administered either in a single treatment or in a series of doses, the success of which will depend on the production of a desired immunological result (i.e., successful production of a CTL-mediated response to the antigen, which response gives rise to the prevention and/or treatment desired). Thus, the overall administration schedule must be considered in determining the success of a course of treatment and not whether a single dose, given in isolation, would or would not produce the desired immunologically therapeutic result or effect.

The therapeutically effective amount of a composition containing one or more of the immunogens of this invention, is an amount sufficient to induce an effective CTL response to prevent, cure or arrest disease progression. Thus, this dose will depend, among other things, on the identity of the immunogens used, the nature of the disease condition, the severity of the disease condition, the extent of any need to prevent such a condition where it has not already been detected, the manner of administration dictated by the situation requiring such administration, the weight and state of health of the individual receiving such administration, and the sound judgment of the clinician or researcher. Thus, for purposes of prophylactic or therapeutic administration, effective amounts would generally lie within the range of from 1.0 µg to about 5,000 µg of peptide for a 70 kg patient, followed by boosting dosages of from about 1.0 µg to about 1,000 µg of peptide pursuant to a boosting regimen over days, weeks or months, depending on the recipient's response and as necessitated by subsequent monitoring of CTL-mediated activity within the bloodstream. Of course, such dosages are to be considered only a general guide and, in a given situation, may greatly exceed such suggested dosage regimens where the clinician believes that the recipient's condition warrants more aggressive administration schedule. The efficacy of administering additional doses, and of increasing or decreasing the interval, may be re-evaluated on a continuing basis, in view of the recipient's immunocompetence (for example, the level of CTL activity with respect to acute or chronic DV infection).

For such purposes, the immunogenic compositions according to the present invention may be used against a DV infection by administration to an individual by a variety of routes. The composition may be administered parenterally or orally, and, if parenterally, either systemically or topically. Parenteral routes include subcutaneous, intravenous, intradermal, intramuscular, intraperitoneal, intranasal, transdermal, or buccal routes. One or more such routes may be employed. Parenteral administration can be, for example, by bolus injection or by gradual perfusion over time.

Generally, vaccines are prepared as injectables, in the form of aqueous solutions or suspensions. Vaccines in an oil base are also well known such as for inhaling. Solid forms that are dissolved or suspended prior to use may also be formulated. Pharmaceutical carriers, diluents and excipients are generally added that are compatible with the active ingredients and acceptable for pharmaceutical use. Examples of such carriers include, but are not limited to, water, saline solutions, dextrose, or glycerol. Combinations of carriers may also be used. These compositions may be sterilized by conventional, well known sterilization techniques including sterile filtration. The resulting solutions may be packaged for use as is, or the aqueous solutions may be lyophilized, the lyophilized preparation being combined with sterile water before administration. Vaccine compositions may further incorporate additional substances to stabilize pH, or to function as adjuvants, wetting agents, or emulsifying agents, which can serve to improve the effectiveness of the vaccine.

The concentration of the CTL stimulatory peptides of the invention in pharmaceutical formulations are subject to wide variation, including anywhere from less than 0.01% by weight to as much as 50% or more. Factors such as volume and viscosity of the resulting composition must also be considered. The solvents, or diluents, used for such compositions include water, dimethylsulfoxide, PBS (phosphate buffered saline), or saline itself, or other possible carriers or excipients.

The immunogens of the present invention may also be contained in artificially created structures such as liposomes, ISCOMS, slow-releasing particles, nanoparticles of metal or polymers and other antigen delivery vehicles which increase the immunogenicity and/or half-life of the peptides or polypeptides in serum. Liposomes include emulsions, foams, micelles, insoluble monolayers, liquid crystals, phospholipid dispersions, lamellar layers and the like. Liposomes for use in the invention are formed from standard vesicle-forming lipids which generally include neutral and negatively charged phospholipids and a sterol, such as cholesterol. The selection of lipids is generally determined by considerations such as liposome size and stability in the blood. Liposomes or various nanoparticles containing the peptides or polypeptides of the invention can be directed to the site of lymphoid cells where they deliver the selected immunogens directly to antigen presenting cells. Targeting can be achieved by incorporating additional molecules such as proteins, peptides, oligonucleotides or polysaccharides or synthetic molecules into the outer membranes or incorporate into of said structures, thus resulting in the delivery of the structures to particular areas of the body, or to particular cells within a given organ or tissue. Such targeting molecules may a molecule that binds to receptor on antigen presenting cells. For example an antibody that binds to CD80 could be used to direct antigen delivery carriers to dendritic cells.

The immunogens of the present invention may also be administered as solid compositions. Conventional nontoxic solid carriers including pharmaceutical grades of mannitol, lactose, starch, magnesium, cellulose, glucose, sucrose, sodium saccharin, and the like. Such solid compositions will often be administered orally, whereby a pharmaceutically acceptable nontoxic composition is formed by incorporating the peptides and polypeptides of the invention with any of the carriers listed above. Generally, such compositions will contain 10-95% active ingredient, and more preferably 25-75% active ingredient.

Aerosol administration is also an alternative, requiring only that the immunogens be properly dispersed within the aerosol propellant. Typical percentages of the peptides or polypeptides of the invention are 0.01%-20% by weight, preferably 1%-10%. The use of a surfactant to properly disperse the immunogen may be required. Representative surfactants include the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1-20% by weight of the composition, preferably 0.25-5%. Typical propellants for such administration may include esters and similar chemicals but are by no means limited to these. A carrier, such as lecithin for intranasal delivery, may also be included.

The peptides and polypeptides of the invention may also be delivered with an adjuvant. Adjuvants include, but are not limited to, complete or incomplete Freund's adjuvant, Montanide ISA-51, Activation Gene-3 (LAG-3), aluminum phosphate, aluminum hydroxide, alum, and saponin. Adjuvant effects can also be obtained by injecting a variety of cytokines along with the immunogens of the invention. These cytokines include, but are not limited to IL-1, IL-2, IL-7, IL-12, and GM-CSF. Adjuvant effects can also be obtained by injecting variety of Toll Like Receptor (TLR) agonists or antagonists along with the immunogens of the invention. These TLR ligands include TLR 1-9 ligands, but are not limited to lipopeptides, double or single stranded DNA oligonucleotides with or without CPG DNA motifs, endotoxin and flagellin.

The present invention is also directed to a vaccine in which an immunogen of the present invention is delivered or administered in the form of a polynucleotide encoding the a polypeptide or active fragment as disclosed herein, whereby the peptide or polypeptide or active fragment is produced in vivo. The polynucleotide may be included in a suitable expression vector and combined with a pharmaceutically acceptable carrier. For example, the peptides or polypeptides could be expressed in plasmid DNA and nonreplicative viral vectors such as vaccinia, fowlpox, Venezuelan equine encephalitis virus, dengue virus (e.g., as a part of the chimeric vaccine formulation), adenovirus, or other RNA or DNA viruses. These examples are meant to be illustrative only and should not be viewed as self-limiting. A wide variety of other vectors are available and are apparent to those skilled in the art from the description given herein. In this approach, a portion of the nucleotide sequence of the viral vector is engineered to express the peptides or polypeptides of the invention. Vaccinia vectors and methods useful in immunization protocols are described in U.S. Pat. No. 4,722,848, the disclosure of which is incorporated herein by reference in its entirety.

Regardless of the nature of the composition given, additional vaccine compositions may also accompany the immunogens of the present invention. Thus, for purposes of preventing or treating DV infection (e.g., prophylactic or therapeutic vaccine), compositions containing the immunogens disclosed herein may, in addition, contain other vaccine pharmaceuticals. The use of such compositions with multiple active ingredients is left to the discretion of the clinician.

While the examples are provided below to illustrate the invention, it is to be understood that these methods and examples in no way limit the invention to the embodiments described herein and that other embodiments and uses will no doubt suggest themselves to those skilled in the art. All publications, patents, and patent applications cited herein are hereby incorporated by reference, as are the references cited therein. It is also to be understood that throughout this disclosure where the singular is used, the plural may be inferred and vice versa and use of either is not to be considered limiting.

Example 1: Identification of Dengue Virus Specific CD8+ T Cell Epitopes by Nano LC/MS/MS Methods Patient Samples PBLs from patients previously infected with dengue virus were obtained from Drs. Eduardo Nascimento and Paolo Piazza (University of Pittsburgh). PBLs from patients 82, 28, 102, 69, 139, 151, and 200 were used to assess the presence of circulating dengue specific CD8+ T cells. PBLs from patients PD-026, -039, -043, and -052 were used to assess presence and functionality of these dengue virus specific CD8+ T cells in T cell based assays as described below. Patients ranged from 21-50 years of age. All patients were determined to be seropositive for previous dengue virus infections via serology (i.e. Dengue IgG positive).

Cells and Viruses

The HLA-A2 and A24 positive liver hepatocellular carcinoma cell line was cultured in Dulbecco's Modified Eagle Medium/Ham's F-12 50/50 Mix (Mediatech Inc, Manassas Va.). The B cell lymphoblastoid line JY (HLA-A2) and the lung carcinoma cell line HTB-177 (HLA-A24) were grown in RPMI-1640. All media was supplemented with 10% fetal bovine serum (Atlanta Biologicals, Flowery Branch, Ga.), L-glutamine (300 mg/mL), 1x non-essential amino acids, 0.5 mM sodium pyruvate, and 1x penicillin/streptomycin (Mediatech Inc). Cell lines were maintained at 37° C. and 5% $CO_2$.

Dengue virus 2 (serotype 2, strain 16681) was a kind gift of Dr. Alex Birk (Cornell University). JY or HTB-177 cells were infected with DENV-2 at an MOI of 5 for one hour, washed extensively, and cultured for 72 hours prior to use in downstream assays.

Isolation, Purification, and Fractionation of MHC class I Bound Peptides Dengue virus specific MHC class I restricted peptides were isolated as previously described. Briefly, $1\times10^9$ DENV-2 infected HepG2 cells were lysed (150 mM NaCl, 10 mM $Na_2HPO_4$, 1 mM EDTA, 1% NP40) and peptide/MHC complexes (p/MHC) were immunoprecipitated using protein A/G beads (UltraLink Immobilized Protein A/G, Pierce, Rockford, Ill.) coated with W6/32, a monoclonal antibody recognizing pan-MHC class I molecules. Antibody coated beads were incubated with cell lysate for 2 hours with rocking followed by a centrifugation step to separate the beads from lysate (1000 rpm/5 min). The p/MHC complexes were eluted from the beads using 0.1% trifluoroacetic acid and the peptides were dissociated from the MHC molecules by heating at 85° C. for 15 minutes. The mixture was cooled and the peptides separated using an Amicon Ultra-3 kDA filter (Millipore, Billerica, Mass.). The resulting peptide mixture was then fractionated using a C-18 reversed phase (RP) column on an offline 3000 HPLC (Dionex).

Mass Spectrometry Analysis

Mass spectrometry experiments were carried out using Orbitrap instruments (Thermo Electron, San Jose, Calif.) interfaced with nano ultimate high-performance liquid chromatography (HPLC; Dionex). RP-HPLC-purified peptide fractions were injected individually into the LC-MS/MS system to identify the sequences [14, 26] of the peptides. The peptides were concentrated using a 300 μm ID×5 mm C18 RP trap column (Dionex) and separated using a 75 μm ID×15 cm C18 RP analytical column (Dionex), equilibrated in 4% ACN/0.1% FA at 250 nL/minute flow rate. Mobile phase A was 2% ACN and 0.1% FA in water, whereas mobile phase B was 0.1% FA and 90% ACN in water. Peptides were separated with a gradient of 4%/50% B in 60 minutes and 50%-80% in 90 minutes and eluted directly into the mass spectrometer. Peptides were analyzed using a data-dependent method. The acquired spectra data were searched against HBV protein database using Proteome Discoverer 1.3 (Thermo) to interpret data and derive peptide sequences. The database search parameters were: enzyme-no enzyme, threshold-100, peptide tolerance-20 ppm, fragment ion tolerance-0.8 Da. The search results were filtered with XCorr according to individual peptide charge status (+1:1.6, +2:1.8, and +3:2.0) and the results were also verified manually to confirm the correct peptide sequence.

Peptide Validation by Synthetic Peptides

Synthetic peptides for validating the peptides identified in this study were obtained from Genscript Corporation and China peptides Co., Ltd. The synthetic peptides were subjected to LC-MS/MS analysis under identical experimental conditions as described above, and their sequences were confirmed based on their MS/MS data. Candidate peptide sequences were confirmed by comparison of MS/MS spectra with synthetic analogues.

Generation of Epitope Specific CTLs In Vitro

Epitope specific $CD8^+$ T cells (CTLs) were generated as previously described. Briefly, PBMCs were isolated from heparinized blood of healthy HLA-A2$^+$ donors (Research BC, LLC, Boston Mass.) using lymphocyte separation medium (Corning, Corning, N.Y.) and cultured in 6-well plates overnight in RPMI-1640. After an overnight incubation, non-adherent cells in the culture were harvested and saved and the adherent cells were pulsed with MHC class I restricted synthetic peptides (50 μg)+β2 microglobulin (1.5 μg) in order to selectively expand epitope specific CTLs. Two hours after pulsing, the non-adherent cells were added back into the plates in a cytokine rich medium of RPMI-1640 supplemented with IL-7 (5 ng/mL), GM-CSF (25 ng/mL), IL-4 (50 ng/mL), and keyhole limpet hemocyanin (5 ug/mL KLH; Sigma-Aldrich) and cultured at 37° C. at 5% CO2. T cells in the culture were restimulated two weeks after the initial stimulation with autologous PBMCs depleted of CD4+ and $CD8^+$ T cells and pulsed with synthetic peptides (10 ug/mL) and β2-microglobulin (1.5 ug/mL). Restimulated cells were cultured in RPMI-1640 supplemented with IL-15 (5 ng/mL), GM-CSF (12.5 ng/mL) and IL-2 (10 U/mL) for 7 days. Restimulation was performed a total of three times prior to CTL functional assays. Unless otherwise specified, all cytokines and growth factors were purchased from eBiosciences (San Diego, Calif.).

Expansion of pre-existing CTLs from seropositive donors was done as previously reported. Briefly, PBLs were isolated from blood from seropositive HLA-A2$^+$ or HLA-A24$^+$ donors, pulsed with 1 ug/mL of synthetic peptides, and cultured in 24 well plates for one week (37° C. 5% CO2). After three days, the culture was supplemented with IL-2 (concentration added here).

ELISpot Assays 96 well PVDF-membrane plates (Millipore) were coated with IFN-gamma capture antibody overnight at 4° C. On the day of the assay, the plates blocked for 2 hours in RPMI-1640 complete medium and washed prior to use in the ELISpot assay. Peptide specific CTLs were harvested, counted, and cultured overnight with appropriate antigen presenting cells (JY or HTB-177 cells) that were unpulsed or pulsed with synthetic peptides or infected with DENV-2. The next day the assay was developed according to the manufactures instructions (BD Biosciences, San Jose, Calif.). Developed spots were quantified using the ELISpot Reader System (AID, San Diego, Calif.).

Results

Vaccines designed to protect against primary and secondary dengue virus infections must induce a robust, multifunctional, and cross-protective $CD8^+$ T cell response. A number of DENV specific $CD8^+$ T cell activating epitopes have been reported; however, these epitopes have been generated using peptide prediction algorithms and therefore may not accurately represent the natural peptides presented on MHC class I molecules during an active infection. In addition, in order for a vaccine formulation to be universally applicable (i.e. protective for multiple populations), it must contain peptide epitopes capable of activating a number of HLA restricted T cell specificities (i.e. contain peptides that bind to different HLA alleles). In order to identify naturally processed and presented MHC class I restricted epitopes that fit these criteria, we utilized an immunoproteomic approach in which peptides associated with MHC class I molecules are isolated from infected cells and identified using mass spectrometry. We previously described four novel HLA-A2 restricted dengue specific epitopes capable of activating cross-reactive CD8+ T cells. We extended these observations to identify epitope restricted to a different HLA molecule using the HLA-A2 expressing cell line HTB-177. Using the immunoproteomic technique, we have identified four additional, novel dengue specific epitopes with high confidence (Table 1).

TABLE 1

MHC class I associated T cell epitopes presented by the dengue virus infected cells

| Seq ID | Peptide | Protein | Accession ID |
|---|---|---|---|
| 1 | AMLCIPNAII | NS2A | C4NAT0 |
| 2 | LLCVPNIMI | NS2A | A8IWB1 |
| 3 | AFIAFVRF | Capsid | AY593217.1 |
| 4 | MIIVDEAHF | NS3 | F6KGX7 |
| 5 | IVFFVLMM | Envelope glycoprotein | M9T2M4 |
| 6 | LLTAIAPSMA | Membrane glycoprotein | Q9W8I3 |
| 7 | LVMVGVITLY | Envelope glycoprotein | Q8JTL5 |
| 8 | VLTGATEIQT | Envelope protein | Q2XS30 |
| 9 | VLVGFVTLYL | Envelope protein | Q9IZJ4 |
| 10 | VVIFILLML | Envelope protein | Q7T4P2 |
| 11 | KLCEDTITY | Capsid | B7U636 |
| 12 | KYQLAVTIMT | NS2A | U3LXC7 |
| 13 | GRLITANPMVT | Envelope glycoprotein | A0EVV8 |
| 14 | TLILAPTRV | NS3 | B4X9Q3 |
| 15 | ITLLCLIPT | Capsid | I7B7U6 |
| 16 | ITLLVKLAL | NS2B | NP_740320 |

Two of these peptides associate with HLA-A24 molecules (MII, AII) and two peptides show promiscuity to binding both HLA-A2 and HLA-A24 molecules (LLC, AML). Interestingly, one of the HLA-A2 epitopes we previously described (KLA) also shows promiscuity to binding HLA-A24. HLA binding affinities were calculated using the SYPFETHI database. We confirmed the identity of these peptides using synthetic analogues. The MS/MS spectra of these analogues matched the spectra of the experimentally identified epitopes nearly identically (data not shown).

Dual Binding Epitopes Identified by MS/MS Activate CTLs In Vitro

After confirming that seropositive patients had functional DENV specific CD8+ T cells in circulation (data not shown), we turned our attention to the four novel, experimentally identified peptides described above (LLC, AML, MII, AFI). As we have done in the past, we first sought to determine if these epitopes could activate CD8+ T cells in vitro in a seronegative patient. PBMCs were isolated from the blood of a healthy HLA-A2 donor and epitope specific CTLs were generated using synthetic peptides. Culturing epitope specific CD8+ T cells with antigen presenting cells (JYs) pulsed with peptides or infected with dengue virus resulted in specific T cell activation, as measured by IFN-gamma secretion (FIG. 1A). Additionally, these CTLs displayed evidence of cytotoxic activity-upregulation of the degranulation marker CD107a and secretion (FIG. 1B) of granzyme B (FIG. 1C).

Figure 2:
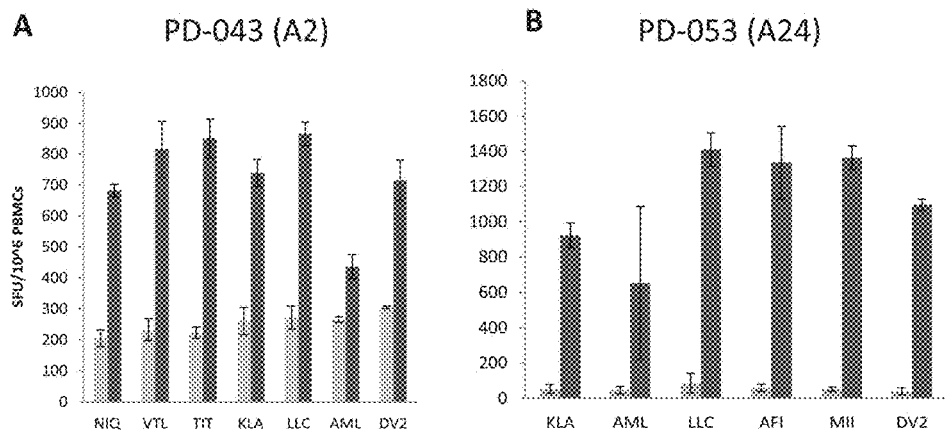
FIG. 2. HLA-A2 and A24 binding dengue virus specific epitopes induce functional responses in seropositive patients in both an HLA-A2 and HLA-A24 specific manner. HLA-A2 (PD-043) or HLA-A24 (PD-053) expressing PBLs were obtained from dengue seropositive patients and stimulated with the corresponding A2, A24, or A2/A24 restricted peptides for 7 days. Cells were harvested, washed, and cultured with peptide pulsed or DENV-2 infected JY (A2) or HTB-177 (A24) cells in an IFN-gamma ELISpot overnight (A, B).

Functional Epitope Specific CD8+ T Cells can be Activated in Seropositive Patients Having confirmed that the experimentally identified epitopes are capable of inducing CD8+ T cell activation (FIG. 1), we wanted to determine if patients who have recovered from dengue virus infection had detectable levels of these epitope specific CD8+ T cells. PBLs were obtained from HLA-A2 and HLA-A24 seropositive donors and stimulated with synthetic peptides. All peptides tested induced specific CD8+ T cell responses in an IFN-gamma ELISpot assay (FIG. 2). Importantly, the dual binding peptides KLA, LLC, and AML induced CD8+ T cell responses in both HLA-A2 positive (FIG. 2A) and HLA-A24 positive (FIG. 2B) individuals in both an HLA-A2 and HLA-A24 restricted manner. Both CD8+ T cells from the HLA-A2 donor and the HLA-A24 donor secreted these cytotoxic molecules after stimulation indicating that these peptides are bona fide dual binders.

Figure 3:
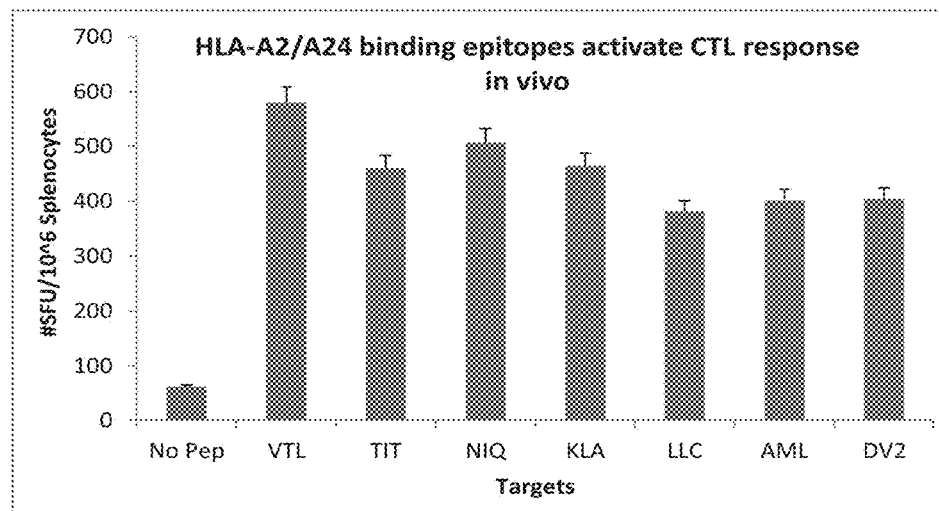
FIG. 3. In vivo CTL response generated by HLA-A2 and A24 binding dengue virus specific T cell epitopes. Human HLA-A2 transgenic mice were injected with a pool of HLA-A2 and A24 binding peptides mixed with montanide 51 adjuvant 3 times and splenocytes were harvested and analyzed for CTL activation using peptide loaded and DV2 infected target cells.

HLA-A2 and A24 Binding Dengue Virus Specific T Cell Epitopes Activate CTL In Vivo CTL activation induced by the dual binding peptides were assessed in human HLA-A2 transgenic mice. Mice were injected with a pool of HLA-A2 and A24 binding peptides mixed with montanide 51 adjuvant 3 times by subcutaneous and intradermal injections. Ten days post last injection, the splenocytes were harvested and analyzed for CTL activation using peptide loaded and DV2 infected target cells. As illustrated in FIG. 3, the dual binding peptides generated a robust CTL response against peptide loaded targets in addition to DV2 infected target cells.

Discussion

Protection from dengue virus infection requires a robust, broad, and multi-functional CD8+ T cell response. Therefore, T cell vaccine formulations must include epitopes or antigens that are a) derived from each of the four serotypes and/or b) conserved throughout the viruses and capable of inducing cross-reactive T cell responses. Most attempts at identifying DENV specific MHC class I restricted epitopes have utilized peptide prediction approaches followed by confirmation through stimulation of T cells derived from healthy or infected individuals. This method has identified a wide range of epitopes associated with multiple HLA alleles and identified the NS3 and NS5 proteins as the most immunodominant regions for specific CD8+ T cell responses. Despite their ability to activate PBLs in vitro, these predicted peptides have not been demonstrated to be presented on the surface of a DENV infected cell. As such, peptides identified by these methods may not accurately represent those epitopes presented on the surface of infected cells in vivo, and their identification is not a guarantee that these peptides are bona-fide T cell activators (unpublished observations). Using an immunoproteomic approach to identify novel epitopes that are naturally processed and presented on the surface of infected cells, we previously identified four epitopes capable of binding to the HLA-A2 molecule and inducing cross-reactive CD8+ T cell responses. Building on that work, in this study we have identified four additional, novel peptides: two peptides (MII and AFI) that associate with the HLA-A24 molecule and two peptides (LLC and AML) that are dual binders, associating with both HLA-A2 and HLA-A24. Importantly, these naturally processed epitopes are derived from a wide range of viral proteins including capsid, NS2A, NS3, NS4B, and NS5

(Table 1) indicating that the peptides presented during a natural infection are derived from the entirety of the viral proteome. Further, a number of these proteins are well conserved between dengue virus subtypes, in particular the non-structural proteins, indicating that these regions are likely to contain multiple CD8+ T cell epitopes.

The immunoproteomic approach to identifying naturally processed and presented MHC class I restricted epitopes allows for the selection and characterization of the most physiologically relevant peptides. In order for these peptides to be included in vaccine formulation, it is important to confirm that these epitopes induce T cell responses in both seropositive as well as seronegative individuals. Importantly, the peptides capable of binding to both HLA-A2 and HLA-A24 molecules induced robust CD8+ T cell responses in both an HLA-A2 and an HLA-A24 seropositive patient, indicating that these peptides are bona-fide dual binders. This latter result has considerable implications-PBLs isolated from patients with documented primary or secondary dengue viral infections respond to the same peptide epitopes despite differences is HLA expression.

There is a definitive need for a vaccine to combat dengue virus infection, yet no formulation has demonstrated significant protective efficacy in clinical trials. Currently, it is hypothesized that live attenuated vaccines may be the most relevant for inducing protective response, most likely because these formulations allow for processing and presentation of a significant portion of the viral proteome. A suitable alternative to the live attenuated approach, then, is the development of a peptide based vaccine comprised of naturally processed and presented class I (and/or class II) restricted epitopes identified by screening infected cells. The immunoproteomic approach to peptide epitope discovery has several significant advantages over peptide prediction algorithms. First and foremost, this approach allows for the identification of epitopes that are present on the surface of the infected cell. In contrast, prediction algorithms sort potential peptides based on a predicted binding score. Most often, only the top scoring or dominant peptides are chosen for follow up studies but it is likely that the epitopes naturally associated with class I molecules do not fit such straightforward criteria. Indeed, we have demonstrated that subdominant peptides are presented by infected or cancerous cells and capable of inducing robust T cell responses, peptides that would have been missed with such stringent cutoffs. Secondly, the immunoproteomic approach allows for the identification of peptides that are capable of binding to multiple HLA alleles (i.e. binding to different members within a supertype), a feature that is underwhelming in peptide prediction algorithms. Finally, peptides binding to different HLA molecules can be identified from the same preparation of infected cells without increasing experimental difficulty. These basic principles: identifying peptides that bind to different HLA alleles and identifying peptides that bind to multiple HLA alleles can be crucial for vaccine formulations as the distribution of these alleles varies significantly worldwide. Including peptides from both arms of the identification process not only provides a more broad coverage for individuals living in endemic areas, it may also increase the breadth and diversity of the T cell response, improving the cross-reactivity and protection from multiple strains of the virus.

Although the present invention has been described with reference to specific embodiments, workers skilled in the art will recognize that many variations may be made therefrom, for example in the particular experimental conditions herein described, and it is to be understood and appreciated that the disclosures in accordance with the invention show only some preferred embodiments and objects and advantages of the invention without departing from the broader scope and spirit of the invention. It is to be understood and appreciated that these discoveries in accordance with this invention are only those which are illustrated of the many additional potential applications that may be envisioned by one of ordinary skill in the art, and thus are not in any way intended to be limiting of the invention. Accordingly, other objects and advantages of the invention will be apparent to those skilled in the art from the detailed description together with the claims.

1. Weaver, S. C. and N. Vasilakis, *Molecular evolution of dengue viruses: contributions of phylogenetics to understanding the history and epidemiology of the preeminent arboviral disease*. Infect Genet Evol, 2009. 9(4): p. 523-40.
2. Whitehorn, J. and C. P. Simmons, *The pathogenesis of dengue*. Vaccine. 29(42): p. 7221-8.
3. Yacoub, S., J. Mongkolsapaya, and G. Screaton, *The pathogenesis of dengue*. Curr Opin Infect Dis. 26(3): p. 284-9.
4. Malavige, G. N. and G. S. Ogg, *T cell responses in dengue viral infections*. J Clin Virol. 58(4): p. 605-11.
5. Weiskopf, D. and A. Sette, *T-Cell Immunity to Infection with Dengue Virus in Humans*. Front Immunol. 5: p. 93.
6. Bhatt, S., et al., *The global distribution and burden of dengue*. Nature. 496(7446): p. 504-7.
7. Mathew, A. and A. L. Rothman, *Understanding the contribution of cellular immunity to dengue disease pathogenesis*. Immunol Rev, 2008. 225: p. 300-13.
8. Bukowski, J. F., et al., *Dengue virus-specific cross-reactive CD8+ human cytotoxic T lymphocytes*. J Virol, 1989. 63(12): p. 5086-91.
9. Simmons, C. P., et al., *Early T-cell responses to dengue virus epitopes in Vietnamese adults with secondary dengue virus infections*. J Virol, 2005. 79(9): p. 5665-75.
10. Mathew, A., et al., *Dominant recognition by human CD8+ cytotoxic T lymphocytes of dengue virus nonstructural proteins NS3 and NS1.2a*. J Clin Invest, 1996. 98(7): p. 1684-91.
11. Hatch, S., et al., *Intracellular cytokine production by dengue virus-specific T cells correlates with subclinical secondary infection*. J Infect Dis. 203(9): p. 1282-91.
12. Yauch, L. E., et al., *A protective role for dengue virus-specific CD8+ T cells*. J Immunol, 2009. 182(8): p. 4865-73.
13. Gil, L., et al., *The cellular immune response plays an important role in protecting against dengue virus in the mouse encephalitis model*. Viral Immunol, 2009. 22(1): p. 23-30.
14. Testa, J. S., et al., *Conserved MHC class I-presented dengue virus epitopes identified by immunoproteomics analysis are targets for cross-serotype reactive T-cell response*. J Infect Dis. 205(4): p. 647-55.
15. Wan, S. W., et al., *Current progress in dengue vaccines*. J Biomed Sci. 20: p. 37.
16. Guirakhoo, F., et al., *Viremia and immunogenicity in nonhuman primates of a tetravalent yellow fever-dengue chimeric vaccine: genetic reconstructions, dose adjustment, and antibody responses against wild-type dengue virus isolates*. Virology, 2002. 298(1): p. 146-59.
17. Dayan, G. H., et al., *Immunogenicity and safety of a recombinant tetravalent dengue vaccine in children and adolescents ages 9-16 years in Brazil*. Am J Trop Med Hyg. 89(6): p. 1058-65.

18. Lindow, J. C., et al., *Vaccination of volunteers with low-dose, live-attenuated, dengue viruses leads to serotype-specific immunologic and virologic profiles*. Vaccine. 31(33): p. 3347-52.
19. Johnson, B. W., et al., *Growth characteristics of ChimeriVax-DEN2 vaccine virus in Aedes aegvpti andAedes albopictus mosquitoes*. Am J Trop Med Hyg, 2002. 67(3): p. 260-5.
20. Vazquez, S., et al., *Immune response to synthetic peptides of dengue prM protein*. Vaccine, 2002. 20(13-14): p. 1823-30.
21. de Melo, A. B., et al., *T-cell memory responses elicited by yellow fever vaccine are targeted to overlapping epitopes containing multiple HLA-I and -II binding motifs*. PLoS Negl Trop Dis. 7(1): p. e1938.
22. Rothman, A. L., *Dengue: defining protective versus pathologic immunity*. J Clin Invest, 2004. 113(7): p. 946-51.
23. Sidney, J., et al., *HLA class I supertypes: a revised and updated classification*. BMC Immunol, 2008. 9: p. 1.
24. Shetty, V., et al., *Quantitative immunoproteomics analysis reveals novel MHC class I presented peptides in cisplatin-resistant ovarian cancer cells*. J Proteomics. 75(11): p. 3270-90.
25. Shetty, V., et al., *MHC class I-presented lung cancer-associated tumor antigens identified by immunoproteomics analysis are targets for cancer-specific T cell response*. J Proteomics. 74(5): p. 728-43.
26. Testa, J. S., et al., *MHC class I-presented T cell epitopes identified by immunoproteomics analysis are targets for a cross reactive influenza-specific T cell response*. PLoS One. 7(11): p. e48484.
27. Weiskopf, D., et al., *Comprehensive analysis of dengue virus-specific responses supports an HLA-linked protective role for CD8+ T cells*. Proc Natl Acad Sci USA. 110(22): p. E2046-53.
28. Khan, A. M., et al., *Conservation and variability of dengue virus proteins: implications for vaccine design*. PLoS Negl Trop Dis, 2008. 2(8): p. e272.
29. Olsen, L. R., et al., *Conservation analysis of dengue virus T-cell epitope-based vaccine candidates using Peptide block entropy*. Front Immunol. 2: p. 69.
30. Betts, M. R., et al., *Sensitive and viable identification of antigen-specific CD8+ T cells by a flow cvtometric assay for degranulation*. J Immunol Methods, 2003. 281(1-2): p. 65-78.
31. Mittendorf, E. A., et al., *Evaluation of the CD107 cytotoxicity assay for the detection of cytolvtic CD8+ cells recognizing HER2/neu vaccine peptides*. Breast Cancer Res Treat, 2005. 92(1): p. 85-93.
32. Parmigiani, A., et al., *Impaired antibody response to influenza vaccine in HIV-infected and uninfected aging women is associated with immune activation and inflammation*. PLoS One. 8(11): p. e79816.
33. Nieminen, J. K., et al., *Dendritic cells from Crohn's disease patients show aberrant STAT1 and STAT3 signaling*. PLoS One. 8(8): p. e70738.

SEQUENCE LISTING

| Seq ID | Peptide | Protein | Accession ID |
|---|---|---|---|
| 1 | AMLCIPNAII | NS2A | C4NAT0 |
| 2 | LLCVPNIMI | NS2A | A8IWB1 |
| 3 | AFIAFVRF | Capsid | AY593217.1 |
| 4 | MIIVDEAHF | NS3 | F6KGX7 |
| 5 | IVFFVLMM | Envelope glycoprotein | M9T2M4 |
| 6 | LLTAIAPSMA | Membrane glycoprotein | Q9W8I3 |
| 7 | LVMVGVITLY | Envelope glycoprotein | Q8JTL5 |
| 8 | VLTGATEIQT | Envelope protein | Q2XS30 |
| 9 | VLVGFVTLYL | Envelope protein | Q9IZJ4 |
| 10 | VVIFILLML | Envelope protein | Q7T4P2 |
| 11 | KLCEDTITY | Capsid | B7U636 |
| 12 | KYQLAVTIMT | NS2A | U3LXC7 |
| 13 | GRLITANPMVT | Envelope glycoprotein | A0EVV8 |
| 14 | TLILAPTRV | NS3 | B4X9Q3 |
| 15 | ITLLCLIPT | Capsid | I7B7U6 |
| 16 | ITLLVKLAL | NS2B | NP_740320 |

I claim:

1. A method for vaccinating and treating a subject for dengue virus infection comprising (i) administering to said subject a composition comprising at least one peptide, oligopeptide or polypeptide that binds to more than one class I MHC allele or can be processed to bind to more than one class I MHC allele and comprises an epitopic peptide comprising an amino acid sequence of SEQ ID NO 2, in an amount sufficient to induce a CTL response to cells infected with dengue virus and expressing one of the more than one class I MHC alleles; or (ii) administering to said subject a composition comprising at least one peptide, oligopeptide or polypeptide that binds to more than one class I MHC allele or can be processed to bind to more than one class I MHC allele and comprises an epitopic peptide having at least one amino acid difference from the amino acid sequence of SEQ ID NO 2, in an amount sufficient to induce a CTL response to cells infected with dengue virus and expressing one of the more than one class I MHC alleles.

2. A method for vaccinating and treating a subject with dengue virus infection said method comprising (i) administering to said subject a composition comprising a polynucleotide comprising a nucleic acid sequence encoding at least one peptide, oligopeptide or polypeptide that binds to more than one class I MHC allele or can be processed to bind to more than one class I MHC allele and comprises the amino acid sequence of SEQ ID NO 2, in an amount sufficient to induce a CTL response to cells infected with dengue virus and expressing one of the more than one class I MHC alleles; or (ii) administering to said subject a composition comprising a polynucleotide comprising a nucleic acid sequence encoding at least one peptide, oligopeptide or polypeptide that binds to more than one class I MHC allele or can be processed to bind to more than one class I MHC allele and comprising an epitopic peptide comprising one amino acid difference from the amino acid sequence of SEQ ID NO 2, in an amount sufficient to induce a CTL response to cells infected with dengue virus and expressing one of the more than one class I MHC alleles.

3. A method for generating an immune response ex vivo using T cells from a subject infected with dengue virus, said method comprising: stimulating the production of CTL response for use in passive immunotherapy, wherein said T cells react with at least one peptide, oligopeptide or polypeptide comprising an amino acid sequence of SEQ ID NO 2; or at least one peptide, oligopeptide or polypeptide comprising one amino acid difference from an amino acid sequence of SEQ ID NO 2.

4. The method of claim 3, wherein said T cells for use in passive immunotherapy are generated from autologous or HLA matched subjects.

5. A method for assessing or diagnosing an immune response in a subject infected with dengue virus or vaccinated for dengue and related viruses said method comprising: stimulating the production of CTL response, wherein said T cells react with at least one peptide, oligopeptide or polypeptide comprising the amino acid sequence of SEQ ID NO 2; or at least one peptide, oligopeptide or polypeptide comprising one amino acid difference from the amino acid sequence of SEQ ID NO 2.

6. A method for vaccinating humans against Dengue virus infection using SEQ ID NO 2 in any delivery system appropriate to generate a vaccine response.

* * * * *